(12) United States Patent
Offerman et al.

(10) Patent No.: US 7,309,592 B2
(45) Date of Patent: Dec. 18, 2007

(54) ETHANOL PRODUCTION FROM BIOLOGICAL WASTES

(75) Inventors: John D. Offerman, Orono, MN (US); Delman R. Hogen, Spring Lake Park, MN (US); Jeffrey W. Lighthart, Minnetonka, MN (US); Hugh McTavish, Birchwood, MN (US)

(73) Assignee: Novus Energy, LLC, Minnetonka, MN (US)

( * ) Notice: Subject to any disclaimer, the term of this patent is extended or adjusted under 35 U.S.C. 154(b) by 320 days.

(21) Appl. No.: 11/137,874

(22) Filed: May 26, 2005

(65) Prior Publication Data

US 2005/0266540 A1 Dec. 1, 2005

Related U.S. Application Data

(60) Provisional application No. 60/574,698, filed on May 26, 2004.

(51) Int. Cl.
C12P 7/06 (2006.01)
C12P 7/08 (2006.01)
C12O 5/00 (2006.01)

(52) U.S. Cl. .................. 435/161; 435/163; 435/166

(58) Field of Classification Search ............... 435/161, 435/163, 166
See application file for complete search history.

(56) References Cited

U.S. PATENT DOCUMENTS

| | | | |
|---|---|---|---|
| 4,235,801 A | 11/1980 | Bhasin | |
| 4,333,852 A | 6/1982 | Warren | |
| 4,492,772 A | 1/1985 | Ball et al. | |
| 4,675,344 A | 6/1987 | Conway et al. | |
| 4,758,600 A | 7/1988 | Arimitsu et al. | |
| 5,173,429 A * | 12/1992 | Gaddy et al. | 435/252.7 |
| 5,185,079 A | 2/1993 | Dague | |
| 5,543,049 A | 8/1996 | Hogen et al. | |
| 5,620,893 A | 4/1997 | Hogen et al. | |
| 5,667,673 A | 9/1997 | Hogen et al. | |
| 5,821,111 A * | 10/1998 | Grady et al. | 435/252.5 |
| 6,136,577 A * | 10/2000 | Gaddy | 435/161 |
| 6,248,796 B1 | 6/2001 | Jackson et al. | |
| 6,340,581 B1 * | 1/2002 | Gaddy | 435/140 |
| 6,509,180 B1 * | 1/2003 | Verser et al. | 435/161 |
| 6,824,682 B2 | 11/2004 | Branson | |
| 2003/0211585 A1 * | 11/2003 | Gaddy et al. | 435/161 |

FOREIGN PATENT DOCUMENTS

EP 0 235 886 A2 9/1987
EP 0 253 540 A1 1/1988
WO WO 03/042117 A1 5/2003

OTHER PUBLICATIONS

Bao, J. et al., 2003, A highly active K-Co-Mo/C catalyst for mixed alcohol synthesis from CO and $H_2$. Chem. Commun. 2003:746-747.
Matsuzaki, T. et al., 1993, Effect of transtion metals on oxygenates formation from syngas over $Co/SiO_2$. Applied Catalysis A: General 105:159-184.
Ehwald, H. et al., 1991, A bicomponent catalyst for the selective formation of ethanol from synthesis gas. Applied Catalysis 76: 153-169.
Pereira, E.B. et al., 1993, Alcohol synthesis from syngas over nickel catalysts: effect of copper and lithium addition. Applied Catalysis A: General 103:291-309.
Bredwell, M.D. et al., 1999, Reactor design issues for synthesis gas fermentations. Biotechnol. Prog. 15:834-844.
Worden, R.M. et al., 1991, Production of butanol and ethanol from synthesis gas via fermentation. Fuel 70: 615-619.
Sun, X and G.W. Roberts, 2003, Synthesis of higher alcohols in a slurry reactor with cesium-promoted zinc chromite catalyst in decahydronaphthalene. Applied Catalysis A: General 247:133-142.
Smith, K.J., C.-W. Young, R.G. Herman, and K. Klier, 1991, Development of a kinetic model for alcohol synthesis over a cesium-promoted Cu/ZnO catalyst. Ind. Eng. Chem. Res. 30:61-71.
Burcham, M.M. et al., 1998, Higher alcohol synthesis over double bed $Cs-Cu/ZnO/Cr_2O_3$ catalysts: optimizing the yields of 2-methyl-1-propanol (isobutanol). Ind. Eng. Chem. Res. 37:4657-4668.
Beretta, A. et al., 1996, Production of methanol and isobutyl alcohol mixtures over double-bed cesium-promoted $Cu/ZnO/Cr_2O_3$ and $ZnO/Cr_2O_3$ catalysts. Ind. Eng. Chem. Res. 35:1534-1542.
Breman, B.B. et al., 1995, Kinetics of the gas-slurry methanol-higher alcohol synthesis from $CO/CO_2/H_2$ over a $Cs-Cu/ZnO/Al_2O_3$ catalyst, including simultaneous formation of methyl esters and hydrocarbons. Catalysis Today 24:5-14.
Beretta, A. et al., 1998, Development of a process for higher alcohol production via synthesis gas. Ind. Eng. Chem. Res. 37:3896-3908.

(Continued)

Primary Examiner—Herbert J. Lilling
(74) Attorney, Agent, or Firm—Cyr & Associates, P.A.

(57) ABSTRACT

The invention provides methods, apparatuses, and kits for producing ethanol and other alcohols. The methods involve fermenting organic material in a fermentation mixture to a biogas comprising methane; converting at least a portion of the biogas to synthesis gas comprising CO and $H_2$; and contacting at least a portion of the synthesis gas with a catalyst to produce alcohol. In some embodiments, a microorganism that reduces ferric iron to ferrous iron is included in the fermentation mixture to enhance the efficiency of the fermentation and the yield of alcohol. The invention also provides a method of producing alcohol involving fermenting organic material to a biogas comprising methane; removing sulfhydryls from the biogas; converting at least a portion of the biogas to synthesis gas comprising CO and $H_2$; contacting at least a portion of the synthesis gas with a sulfur-free catalyst to produce a substantially sulfur-free alcohol; and purifying the alcohol wherein the purified alcohol is substantially sulfur-free and comprises less than 5% methanol and at least 70% $C_2$+ alcohols by weight.

20 Claims, 1 Drawing Sheet

OTHER PUBLICATIONS

Iranmahboob, J. et al., 2003, Dispersion of alkali on the surface of Co-MoS2/clay catalyst: a comparison of K and Cs as a promoter for synthesis of alcohol. *Applied Catalysis A: General* 247:207-218.

Stiles, A.B. et al., 1991, Catalytic conversion of synthesis gas to methanol and other oxygenated products. *Ind. Eng. Chem. Res.* 30:811-821.

Bian, G.-Z. et al., 1998, Mixed alcohol synthesis from syngas on sulfide K-Mo-based catalysts: influence of support acidity. *Ind. Eng. Chem. Res.* 37:1736-1743.

Klasson, K.T. et al., 1993, Biological conversion of coal and coal-derived synthesis gas. *Fuel* 72:1673-1678.

Klasson, K.T. et al., 1992, Biological conversion of synthesis gas into fuels. *Int. J. Hydrogen Energy* 17:281-288.

* cited by examiner

ETHANOL PRODUCTION FROM BIOLOGICAL WASTES

This application claims priority from U.S. provisional patent application Ser. No. 60/574,698, filed May 26, 2004.

BACKGROUND

Disposal of municipal sewage and agricultural waste is often a costly process. Sewage and biological wastes, such as manure, are often disposed of by anaerobic microbial digestion to convert the digestible solid and liquid matter to a biogas composed primarily of $CH_4$ and $CO_2$. The biogas is often burned to avoid releasing the powerful greenhouse gas methane. Sometimes the heat from burning the biogas is used, for instance, to heat buildings or to power turbines and produce electricity. But heat and electricity are low-value products, so usually the disposal process remains a net economic drain.

In addition to failing to produce a high-value product, anaerobic digestion of sewage and biological wastes is frequently slower and more incomplete than would be desired. Anaerobic microbial digestion also produces hydrogen sulfide and other sulfhydryl compounds that corrode metal pipes and fermentation tanks and cause odors that are objectionable to neighbors of the waste-treatment plant.

New methods of disposing of sewage and other biological or organic wastes are needed. Preferably the methods would allow a more complete and efficient conversion of the wastes. Preferably the methods would remove or convert odor-causing compounds. Preferably the methods would produce a higher value product than current methods.

SUMMARY

The invention provides methods and apparatuses for producing alcohol, and in particular ethanol, from biological wastes such as manure, sewage, and crop wastes, as well as from other organic materials. In the methods, organic material is first fermented by anaerobic microorganisms to a biogas consisting primarily of methane and carbon dioxide. The biogas is then converted to synthesis gas consisting primarily of CO and $H_2$. This is typically accomplished by steam reforming or partial oxidation of the methane. The synthesis gas (syngas) is then contacted with a catalyst, such as the ruthenium catalyst described in U.S. Pat. No. 4,333,852, that catalyzes the condensation of CO and $H_2$ to form alcohol—typically mixed alcohols consisting primarily of ethanol. Industrial alcohol is a high value product.

The biggest market for industrial alcohol is as a fuel or a gasoline additive. In these uses it is desirable to have a low concentration of methanol and a high concentration of ethanol and $C_3+$ alcohols in the alcohol mixture. Preferably, the methanol concentration is less than 0.5% and the ethanol concentration is greater than 60% w/w in the alcohol mixture. The alcohols produced by the present methods are also valuable because they contain significant amounts of $C_3+$ alcohols. The $C_3+$ alcohols increase the octane rating of fuels and have more value than ethanol.

The inventors have found that the yield of biogas in the fermentation can be increased by including a microorganism in the fermentation mixture that uses $Fe^{3+}$ as a terminal electron acceptor, reducing it to $Fe^{2+}$, and that converts organic substrates, such as ethanol formed by yeasts, to volatile acids, including acetic acid and typically propionic and butyric acid, as well as potentially formic acid. The iron-reducing microorganism increases the yield of methane and $CO_2$. Although not wishing to be bound by theory, the inventors believe this is because the acids the iron-reducing microorganism forms are efficient substrates for methanogenic microorganisms in the fermentation mixture. By improving the yield of methane, inclusion of the iron-reducing microorganism also improves the yield of alcohol in the overall process. A preferred iron-reducing microorganism is ATCC 55339, described in U.S. Pat. Nos. 5,543,049, 5,620,893, and 5,667,673.

Another advantage of including the iron-reducing microorganism in the fermentation mixture is that it can remove odor-causing compounds. The iron-reducing microorganism converts relatively insoluble $Fe^{3+}$ to the more soluble $Fe^{2+}$. $Fe^{2+}$ binds sulfhydryl groups and precipitates compounds containing sulfhydryls, which are the bulk of odor-causing compounds. Sulfhydryls can also be removed by adding other metal cations, without necessarily adding an iron-reducing microorganism.

The inventors have also discovered that in some embodiments conducting the fermentation with both a thermophilic (45° C. or above) and a mesophilic (below 45° C.) fermentation step improves the yield of biogas in the fermentation, and therefore the yield of alcohol in the process. This may be in part because during the thermophilic step some heat-induced chemical breakdown of the organic materials occurs, and this increases the amount of fermentable material available in the mesophilic step.

The process can also be made more energy efficient by using heat generated in the alocohol-producing catalytic step to heat the fermentation mixture.

When the process involves removing sulfhydryls from the biogas (e.g., with $Fe^{2+}$ formed by the iron-reducing microorganism) and catalyzing alcohol production with a sulfur-free catalyst, the process can produce a substantially sulfur-free alcohol that has particular value as a fuel or fuel additive.

Accordingly, the invention provides a method of producing alcohol comprising: (a) fermenting organic material in a fermentation mixture to a biogas comprising methane; (b) removing sulfhydryls from the biogas; (c) converting at least a portion of the biogas to synthesis gas comprising CO and $H_2$; (d) contacting at least a portion of the synthesis gas with a sulfur-free catalyst to produce alcohol; and (e) purifying the alcohol, wherein the purified alcohol comprises less than 10 ppm sulfur atoms, less than 5% methanol, and at least 70% $C_2+$ alcohols by weight.

Another embodiment of the invention provides a method of producing alcohol involving: (a) fermenting organic material in a fermentation mixture to a biogas containing methane, wherein the fermentation mixture comprises a microorganism that reduces $Fe^{3+}$ and produces at least one volatile organic acid from organic substrates; (b) converting at least a portion of the biogas to synthesis gas containing CO and $H_2$; and (c) contacting at least a portion of the synthesis gas with a catalyst to produce alcohol.

Another embodiment of the invention provides a method of producing alcohol involving: (a) fermenting organic material in a fermentation mixture to a biogas containing methane; (b) removing odiferous compounds from the biogas by contacting the biogas with a metal cation that binds sulfhydryls; (c) converting at least a portion of the biogas to synthesis gas containing CO and $H_2$; and (d) contacting at least a portion of the synthesis gas with a catalyst to produce alcohol.

Another embodiment of the invention provides a method of producing alcohol involving: (a) fermenting organic material in a fermentation mixture to a biogas containing methane; (b) converting at least a portion of the biogas to synthesis gas containing CO and $H_2$; (c) contacting at least a portion of the synthesis gas with a catalyst to produce alcohol; and (d) purifying the alcohol, wherein the purified alcohol contains less than 0.5% by weight methanol. Preferably the alcohol contains at least 70% by weight $C_2+$ alcohols, wherein the yield of $C_2+$ alcohols is at least 6 gallons per 1000 cubic feet of methane in the biogas, and the conversion of volatile organics in the fermentation mixture to biogas is at least 65% efficient.

Another embodiment of the invention provides a method of producing alcohol involving: (a) fermenting organic material in a fermentation mixture to a biogas containing methane, wherein the fermenting involves fermenting for at least 12 hours at a temperature in the range of 45-100° C. followed by fermenting for at least 12 hours at a temperature in the range of 0-44° C.; (b) converting at least a portion of the biogas to synthesis gas containing CO and $H_2$; and (c) contacting at least a portion of the synthesis gas with a catalyst to produce alcohol; wherein the alcohol comprises less than 0.5% by weight methanol.

Another embodiment of the invention provides an apparatus for producing ethanol from organic material, having: (a) a fermentation vessel containing a fermentation mixture that comprises a microorganism that reduces $Fe^{3+}$ and produces at least one volatile organic acid from organic substrates; (a) being functionally coupled to (b) a device for producing synthesis gas comprising CO and $H_2$ from biogas comprising $CH_4$, the device comprising a steam reformer, a partial oxidation unit, or both; (b) being functionally coupled to (c) a catalyst for converting synthesis gas to an alcohol mixture containing $C_2+$ alcohol.

Another embodiment of the invention provides an apparatus for producing ethanol from organic material, having: (a) a fermentation vessel for holding a fermentation mixture and microorganisms that ferment the fermentation mixture to a biogas comprising methane; (a) being functionally coupled to (b) a device for producing synthesis gas comprising CO and $H_2$ from biogas comprising $CH_4$, the device comprising a steam reformer, a partial oxidation unit, or both; (b) being functionally coupled to (c) a catalyst for converting synthesis gas to an alcohol mixture containing $C_2+$ alcohol; (c) being functionally coupled to (d) a purification unit comprising a condenser to preferentially condense at least on C2+alcohol from the alcohol mixture, generating a C2+-rich alcohol fraction and a methanol-rich fraction; and (e) a recirculation unit functionally coupled to (c) and (d) to recirculate at least a portion of the methanol-rich fraction to catalyst (c) for reaction with synthesis gas.

The invention also provides a kit for use in producing ethanol, comprising packaging material containing: (a) a microorganism that reduces $Fe^{3+}$ and produces at least one volatile organic acid from organic materials; and (b) instruction means indicating that the microorganism is to be used in an apparatus for producing ethanol from organic materials by fermenting the organic material to a biogas, converting the biogas to a synthesis gas, and contacting the synthesis gas with a catalyst to produce ethanol.

The invention also provides alcohol products prepared by the processes of producing alcohol of the invention. Among these is a purified alcohol prepared by a process involving (a) fermenting organic material in a fermentation mixture to a biogas comprising methane; (b) removing sulfhydryls from the biogas; (c) converting at least a portion of the biogas to synthesis gas comprising CO and $H_2$; (d) contacting at least a portion of the synthesis gas with a sulfur-free catalyst to produce alcohol; and (e) purifying the alcohol, wherein the purified alcohol comprises less than 10 ppm sulfur atoms, less than 5% methanol, and at least 70% $C_2+$ alcohols by weight.

DETAILED DESCRIPTION

Definitions

Figure 1:
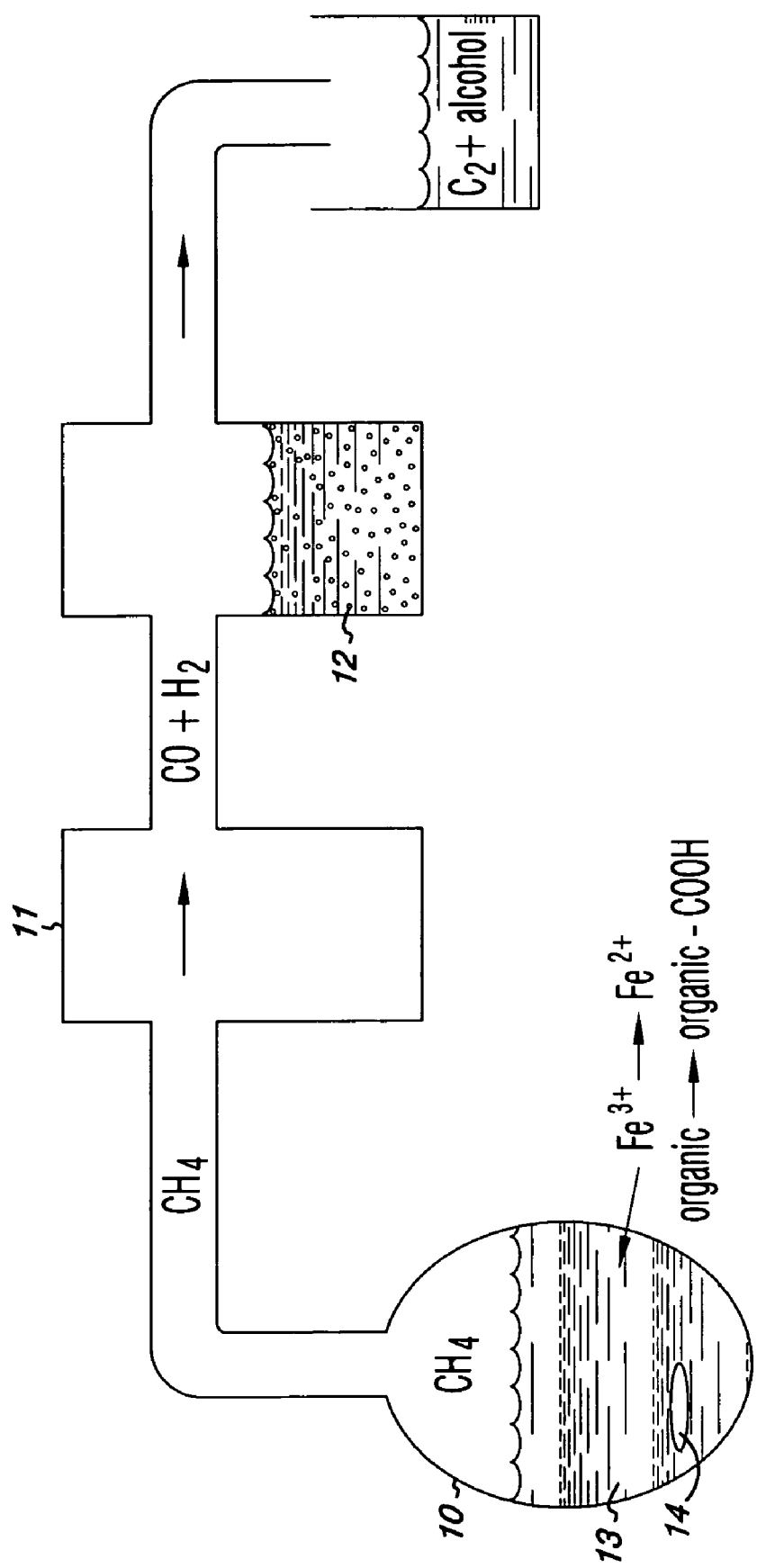
FIG. 1 is a schematic diagram of an apparatus of the invention for producing alcohol from organic material.

"Biogas" as used herein refers to a gas produced by the fermentative anaerobic metabolism of microorganisms. The biogases described herein contain methane and typically contain carbon dioxide as their major constituents.

The term "fermenting" organic material as used herein refers to digestion of the organic material by microorganisms using anaerobic respiration.

The term "partially oxidizing" as used herein refers to incomplete oxidation of a reduced substrate by reaction with oxygen or another oxidizing agent. An example is conversion of methane to a more oxidized compound other than carbon dioxide, e.g., methanol or carbon monoxide. In a particular embodiment, partially oxidizing a biogas involves reacting methane with $O_2$ to produce CO and $H_2$. "Partially oxidizing" the biogas includes partially oxidizing all of the biogas and partially oxidizing a portion of the biogas.

The term "sulfhydryls" as used herein refers to SH groups or to compounds having one or more SH groups. The term "sulfhydryls" includes, e.g., hydrogen sulfide, methanethiol, ethanethiol, and 2-mercaptoethanol.

The term "sulfided, nanosized transition metal catalyst" refers to a catalyst composed primarily of a transition metal or a combination of transition metals, where the particles have a mean particle diameter less than 200 nm, preferably less than 100 nm, and where the metal is sulfided.

The term "volatile organic acid" refers to a compound having a COOH group and containing 6 or fewer carbon atoms. It includes formic acid, acetic acid, propionic acid, and butyric acid.

The terms "$C_2+$ alcohols" and "$C_3+$ alcohols" refer to alcohols having, respectively, two or more and three or more carbons.

The terms "alcohol" and "purified alcohol" produced by the methods of the invention include mixtures of alcohols and mixtures containing alcohols and other components, including in some cases water, aldehydes, ketones, ethers, esters, organic acids, and acid anhydrides. Preferably the alcohol and purified alcohol products of the methods of the invention consist of greater than 50%, more preferably greater than 60%, more preferably greater than 70%, more preferably greater than 80%, more preferably greater than 90%, and more preferably still greater than 95% by weight alcohols.

The term "volatile organics" refers to the mass of material in a biomass that is liquid or solid after drying at 105° C. and gasified after heating to 550° C. in air.

Description

The invention provides methods of producing alcohol involving the steps of (1) fermenting organic material in a fermentation mixture to a biogas containing methane, (2) converting at least a portion of the biogas to synthesis gas containing CO and $H_2$, and (3) contacting at least a portion of the synthesis gas with a catalyst to produce alcohol.

FIG. 1 is a schematic drawing of an apparatus of the invention. The apparatus includes a fermentation vessel 10 holding a fermentation mixture 13. The fermentation mixture includes an iron-reducing microorganism 14 that enhances the efficiency of the fermentation. The iron-reducing microorganism 14 reduces $Fe^{3+}$ and produces at least one volatile organic acid (a compound having a COOH group and 6 or fewer carbon atoms) from organic substrates. The fermentation produces a biogas that includes $CH_4$ and occupies the head space of the fermentation vessel. The biogas comprising $CH_4$ passes to a device 11 for producing synthesis gas containing CO and $H_2$. The device 11 can be or include, for instance, a steam reformer, partial oxidation unit, or both. The synthesis gas passes over and contacts a catalyst 12 to be converted to a $C_2+$ alcohol (e.g., ethanol, propanol, butanol, or a mixture thereof).

In some embodiments of the methods and apparatuses of the invention, the fermentation mixture contains a microorganism that reduces $Fe^{3+}$ and that produces at least one volatile organic acid (typically a mixture of acids containing predominantly acetic acid) from organic substrates. In some embodiments the microorganism produces acetic acid. In some embodiments, the microorganism reduces $Fe^{3+}$ to $Fe^{2+}$. In some embodiments, the microorganism reduces $Fe^{3+}$ to $Fe^{2+}$ and produces acetic acid.

The preferred iron-reducing microorganism is deposited with the American Type Culture Collection under accession number ATCC 55339. Thus, in some embodiments, the microorganism is derived from ATCC 55339. By "derived from ATCC 55339," it is meant that the iron-reducing microorganism grows from the ATCC 55339 culture, is one of the species represented in the culture, or is selected from the culture, e.g., by mutagenesis and selection for an improved strain.

In some embodiments, the microorganism is ATCC 55339.

ATCC 55339 enhances the efficiency of conversion of the organic material to biogas. The conversion efficiency is measured as chemical oxygen demand (COD) destroyed by the fermentation divided by the starting COD of the organic material. This approximates (methane+$CO_2$ produced)/(volatile organics). Volatile organics is defined as the amount of organic material gasified by treatment at 550° C. in air. The inventors have found that fermentation of dairy manure for 12 days at 95° F. using just the native flora found in the manure gives a conversion efficiency of 46-52%. With the addition of ATCC 55339 and magnetite as an iron source, this increases significantly.

ATCC 55339 reduces $Fe^{3+}$ to $Fe^{2+}$ and produces a mixture of volatile acids, including acetic acid, propionic acid, and butyric acid. It can use $Fe^{3+}$ from solution or extract it from an insoluble iron source such as magnetite or taconite.

It is believed that ATCC 55339 enhances the efficiency of fermentation first because it can use a sometimes abundant external electron acceptor, namely $Fe^{3+}$, which enhances the speed and efficiency of breaking down the organic substrates. Second, it is believed to enhance the efficiency of the fermentation because it produces acetic acid and other volatile organic acids, and these are good substrates for the methanogenic archaea (archaebacteria) to convert to $CH_4$ and $CO_2$. Accordingly, while ATCC 55339 is particularly preferred, any microorganism that reduces $Fe^{3+}$ and produces at least one volatile organic acid will enhance the yield of biogas production and therefore the yield of ethanol.

In one embodiment of the invention, the fermentation mixture further contains an iron source. The iron source preferably includes $Fe^{3+}$. In principle, the iron source can be a more reduced form of iron, such as $Fe^0$, and be oxidized in situ to $Fe^{3+}$ by chemical or microbial action. But under anaerobic fermentation conditions, more reduced iron is not expected to be oxidized to $Fe^{3+}$.

Thus, preferably the iron source comprises $Fe^{3+}$. An iron source that comprises $Fe^{3+}$ can involve $Fe^{3+}$ in solution or a complexed insoluble form of iron where some of the iron atoms are in the 3+oxidation state, e.g., magnetite or taconite. In particular embodiments, the iron source is magnetite. In other particular embodiments, it is taconite.

In some embodiments of the methods of the invention, the method involves partially oxidizing the biogas. This increases the ratio of CO to $H_2$ in the syngas as compared to steam reforming the biogas. Partial oxidation of methane produces a ratio of $2H_2$ per CO. Steam reforming produces a ratio of $3H_2$ per CO. The increased CO to $H_2$ ratio from partial oxidation decreases the amount of methanol and increases the amount of ethanol and higher alcohols produced from the syngas.

Methods of partial oxidation are well known, and units for partial oxidation of methane to CO and $H_2$ are commercially available. For instance, partial oxidation can be accomplished by oxygen-starved burning.

In some embodiments of the invention, a portion of the biogas is partially oxidized and a portion is steam reformed. Steam reforming involves the reaction of methane with water vapor at high temperatures and pressures to produce CO and $H_2$. Steam reformers, like partial oxidation units, are commercially available.

In some embodiments of the invention, a portion or all of the biogas is steam reformed.

Fuel alcohol preferably is predominantly higher alcohols. Alcohol mixtures that are too rich in methanol are sensitive to phase separation in the presence of water, which is ubiquitous in gasoline systems. Thus, preferably the alcohol products are rich in $C_2+$alcohols and have low methanol content. In some embodiments the alcohol comprises less than 5% methanol by weight. Preferably the alcohol comprises at least 70% by weight $C_2+$ alcohols. In some embodiments, the alcohol comprises less than 0.5% by weight methanol. In some embodiments, the alcohol comprises at least 60% by weight ethanol. In some embodiments the alcohol comprises less than 0.5% by weight methanol and at least 60% by weight ethanol. In some embodiments, the alcohol comprises at least 92.1% by weight ethanol. In some embodiments, the alcohol comprises at least 5% or at least 10% by weight $C_3+$ alcohols.

Several factors can contribute to obtaining alcohol with a high $C_2+$ alcohol content. One is use of a syngas having a higher ratio of CO to $H_2$. As discussed above, partial oxidation of methane produces a higher CO:$H_2$ ratio than steam reforming.

Another factor involved in obtaining alcohol with a high $C_2+$ alcohol content. is using a catalyst and reaction conditions that promote $C_2+$ alcohol formation over methanol formation. Suitable catalysts include the catalysts described in Bao, J. et al., 2003, *Chem. Commun.* 2003:746-747; U.S. Pat. No. 4,235,801; and U.S. Pat. No. 4,333,852. The catalyst described in Bao et al. is a K—Co—Mo/C catalyst. It is formed by the following procedure. $Co(NO_3)_2$ and $(NH_4)_6Mo_7O_{24}$ aqueous solutions are prepared and mixed at a Co/Mo molar ratio of 0.5. Citric acid is added to the solution under constant stirring (citric acid/metalic ions molar ratio=0.1). Then a $K_2CO_3$ solution is dripped slowly into the solution (K/Mo molar ratio=0.1). The pH value of the solution is adjusted to 3.5 with HCOOH and $NH_4OH$. The solution is kept in a water bath at 65° C. until the solution becomes a gel. The gel is dried at 120° C. for 15 hours and calcined in argon at 400° C. for 4 hours. Suitable reaction conditions with the synthesis gas are a temperature of 230° C., a pressure of 6.0 MPa, and a gas hour space velocity of 9600 hour$^{-1}$. Under these conditions, the CO conversion was 7.5% C, the alcohol selectivity was 60.4% of carbon, the alcohol space-time yield was 296 g per kg-hour, and the $C_2$+alcohol to methanol ratio was 1.48. (Bao, J. et al., 2003, *Chem. Commun.* 2003:746-747.)

Other suitable catalysts are described in U.S. Pat. No. 4,333,852. The catalysts are ruthenium catalysts with a halogen promoter and a phosphine oxide compound as a solvent. An example of catalyst preparation and alcohol synthesis involves the following procedure. 16 milligrams of Ru atoms as triruthenium dodecacarbonyl, 5.6 mmoles of elemental iodine, and 75 ml of tripropylphosphine oxide are placed in a back-mixed autoclave with a net volume of 128 ml and heated with stirring to 55° C. The reactor is pressurized to 500 psi with CO, heated to 240° C., and then pressurized with a $H_2$/CO mixture ($H_2$/CO ratio=2.0) to 6,000 psi. As the reaction proceeds the pressure drops. When it drops to 500 psi, the reactor is repressurized with the synthesis gas to 6,000 psi. With this procedure, ethanol is produced at a rate of 2.05 moles/liter/hour at a selectivity of 50 weight percent. The ethanol plus methanol selectivity is 74 weight percent.

Perhaps the most important mechanism to obtain alcohol with low methanol content and high $C_2$+ alcohol content is to fractionate the alcohol as it is formed into a $C_2$+-rich alcohol fraction and a methanol-rich fraction, harvest the $C_2$+-rich alcohol fraction, and recirculate the methanol-rich fraction into the synthesis gas for contact with the catalyst. Adding methanol to the synthesis gas reaction on the catalyst forces the equilibrium of the $CO+2H_2\longrightarrow CH_3OH$ reaction to the left (Gavin, D. G. and Richard D. G., European Patent Application 0 253 540). With the equilibrium preventing further net formation of methanol, the CO and $H_2$ react to form ethanol and other $C_2$+ products. Recirculated methanol can also be a reactant for formation of $C_2$+ products by reaction with CO, $H_2$, and/or a second molecule of methanol. If all methanol produced is recirculated, there is no net production of methanol.

In the methanol-recirculation process, the alcohol products from the catalyst are fractionated into a $C_2$+-rich alcohol fraction and a methanol-rich fraction. This is preferably done by condensing the $C_2$+ alcohols from the product mixture at a temperature and pressure below the boiling point of the $C_2$+ alcohols and above the boiling point of methanol. The gaseous methanol-rich fraction is then mixed with the synthesis gas for contact with the catalyst.

The alcohols produced in the methods of the invention, including the $C_2$+-rich alcohol fraction separated from the methanol-rich fraction, can be further processed or fractionated. For instance, ethanol can be separated from other alcohols and other components in the mixtures. The mixtures often contain propanol, butanol, and isobutanol, which can be purified. Acetaldehyde, acetic acid, acetic anhydride, and other components may be present in the alcohol mixtures and can be purified or separated from the alcohols.

In some embodiments of the invention, the fermenting involves fermenting for at least 12 hours at a temperature in the range of 45-100° C., followed by fermenting for at least 12 hours at a temperature in the range of 0-44° C. ATCC 55339 is only active at mesophilic temperatures, so if ATCC 55339 is used in the fermentation, it must be used in the fermentation step at a temperature in the range of 0-44° C.

In some embodiments of the invention, the step of contacting the synthesis gas with the catalyst produces heat that is used to heat the fermentation mixture.

In some embodiments of the invention, the iron-reducing microorganism produces $Fe^{2+}$ that binds sulfhydryls in the fermentation mixture and/or in the biogas.

In some embodiments, the step of fermenting organic material to a biogas involves the steps of feeding the organic material into a vessel, fermenting and mixing the organic material in anaerobic conditions in the vessel to form the biogas, discontinuing the mixing to allow particulate unfermented organic material to settle in the vessel resulting in the formation of a low-suspended-solid supernatant, decanting the supernatant from the vessel, and repeating at least the feeding and fermenting steps. This method improves the efficiency of gasification of the organic material, as compared to a two-vessel system (U.S. Pat. No. 5,185,079). In the two-vessel system, fermentation occurs in one vessel and then the wastewater flows to a separate solids separation unit where settling takes place. The settled solids are then recycled to the fermentation vessel (U.S. Pat. No. 5,185,079). The one-vessel system also requires less capital investment.

In one embodiment of the one-vessel method, the method further involves withdrawing at least a portion of the biogas from the vessel, optionally with the use of a vacuum, immediately before the settling step.

In some embodiments of the methods of the invention, the organic material comprises dairy manure. In other embodiments, the organic material comprises hog manure, turkey manure, chicken manure, slaughterhouse waste, municipal sewage, or crop waste. One crop waste suitable for fermenting in the methods of the invention is sugar beet waste (e.g., sugar beet tailings).

In some embodiments, the organic material comprises forest products waste (e.g., sawdust).

In some embodiments of the invention, the fermenting involves fermenting at a temperature in the range of 0-44° C. (with mesophilic organisms). In some embodiments, the fermenting involves fermenting at a temperature in the range of 45-100° C. (with thermophilic organisms).

In some embodiments of the invention, the catalyst is a sulfided, nanosized transition metal catalyst selected from Group VI metals. In some embodiments, the catalyst is a sulfided, nanosized molybdenum catalyst. (U.S. Pat. No. 6,248,796.)

In some embodiments, the sulfided, nanosized transition metal catalyst is suspended in a solvent, e.g., heavy machine oil, and the synthesis gas is contacted with the catalyst at a temperature in the range of 250-325° C. and at a pressure in the range of 500 to 3000 psi.

The catalyst can also be other metal or inorganic catalysts, such as are disclosed in U.S. Pat. Nos. 4,675,344; 4,749,724; 4,752,622; 4,752,623; and 4,762,858.

Preferably, the catalyst is sulfur-free, because a sulfur-containing catalyst leaches sulfur into the alcohol mixtures it produces. Sulfhydryls are undesirable in fuel alcohol because they carry an odor, upon burning they produce sulfur oxides that cause acid rain and human health problems, and they can damage engine parts in internal combustion engines. Thus, preferably the alcohols contain less than 10 ppm sulfur atoms, more preferably less than 1 ppm sulfur atoms. This can be achieved by removing sulfhydryls from biogas before the biogas is converted to synthesis gas, and then using a sulfur-free catalyst for conversion of synthesis gas to alcohol. One method to remove sulfhydryls from biogas is to contact the biogas with a metal cation that binds sulfhydryls, such as $Fe^{2+}$. Another method is to contact the biogas with another type of agent that binds sulfhydryls, such as amine compounds, which may be immobilized on a resin.

Alternatively, sulfhydryls can be removed from the alcohol product. One method to do this is to contact the alcohol with a metal cation that binds sulfhydryls, such as $Fe^{2+}$. Another method is to contact the alcohol with another type of agent that binds sulthydryls, such as amine compounds, which may be immobilized on a resin.

In particular embodiments of the methods and products of the invention, the alcohol or purified alcohol has less than 10 ppm or less than 1 ppm (by weight) sulfur atoms in sulfhydryl compounds. In other embodiments, the alcohol or purified alcohol has less than 10 ppm or less than 1 ppm sulfur atoms (in any form).

The methods of the invention can also involve contacting the biogas with a sulfur scrubber separate from the $Fe^{2+}$ produced by the iron-reducing organism. The sulfur scrubber may remove one or more of sulfhydryls, $H_2S$, anionic oxidized forms of sulfur (e.g., sulfate and sulfite), and COS.

Sulfhydryls and other forms of sulfur can also be removed from the alcohol after it is formed. Thus, one embodiment of the invention provides a method of producing alcohol involving (a) fermenting organic material in a fermentation mixture to a biogas comprising methane; (b) converting at least a portion of the biogas to synthesis gas comprising CO and $H_2$; (c) contacting at least a portion of the synthesis gas with a catalyst to produce alcohol; (d) contacting the alcohol with a scrubber to remove sulfhydryls from the alcohol; and (e) purifying the alcohol, wherein the purified alcohol contains less than 10 ppm sulfur atoms, less than 5% methanol, and at least 70% $C_2+$ alcohols by weight.

In principle, the catalyst for converting syngas to alcohol could be a biological catalyst, such as a microorganism or purified enzyme that converts CO and $H_2$ to ethanol or other alcohols. Some of these are described in Bredwell, M. D., et al., 1999, *Biotechnol. Prog.* 15:834-844; Vega, J. L., et al., 1989, *Appl. Biochem. and Biotech.* 20/21:781; Barik, S. et al., 1988, *Appl. Biochem. and Biotech.* 18:379.

In some embodiments of the methods of the invention, the alcohol includes $C_2+$ alcohols and the yield of $C_2+$ alcohols is at least 4 gallons, at least 5 gallons, or at least 6 gallons per 1000 cubic feet of methane in the biogas.

In particular embodiments of the methods, the conversion of volatile organics in the fermentation mixture to biogas is at least 50%, at least 65%, at least 70%, or at least 75% efficient.

In some embodiment of the methods, the alcohol includes $C_2+$ alcohols and the yield of $C_2+$ alcohols is at least 6 gallons per 1000 cubic feet of methane in the biogas, and the conversion of volatile organics in the fermentation mixture to biogas is at least 65% efficient.

In some embodiments of the invention, the organic material fermented includes cellulose, and the method includes digesting the organic material with cellulase before or during the fermentation step. The cellulase can be an isolated enzyme or cellulase in a cellulase-containing microorganism.

One embodiment of the invention provides a method of producing alcohol comprising: (1) fermenting organic material in a fermentation mixture to a biogas comprising methane, (2) removing odiferous compounds from the biogas by contacting the biogas with a metal cation that binds sulfhydryls, (3) converting at least a portion of the biogas to synthesis gas comprising CO and $H_2$, and (4) contacting at least a portion of the synthesis gas with a catalyst to produce alcohol.

The metal cation that binds sulfhydryls can be $Fe^{2+}$. In some embodiments, the $Fe^{2+}$ is formed by microbial action from iron in other oxidation states. In some embodiments, the microbial action involves reducing $Fe^{3+}$ to $Fe^{2+}$ by an iron-reducing microorganism that produces at least one volatile organic acid from organic substrates.

In other embodiments, the metal cation that binds sulfhydryls is a cation of zinc or copper.

In some embodiments of the methods of the invention, an exogenous microorganism (i.e., an organism in addition to the organisms found in the organic material to be fermented) is added to the fermentation mixture to enhance the efficiency or speed of biogas production.

The alcohols produced by the methods of the invention have an advantage over grain-fermented ethanol as a fuel additive in that the present alcohols include substantial amounts of propanol, n-butanol, iso-butanol, and pentanol. These $C_3+$ alcohols boost the octane of fuel more effectively than ethanol. Thus, in some embodiments of the alcohols produced by processes of the invention, the alcohols include at least 5% or at least 10% $C_3+$ alcohols by weight.

In some embodiments of the apparatuses of the invention, the apparatus includes a purification unit functionally coupled to the catalyst for converting synthesis gas to alcohol, the purification unit comprising a condenser to preferentially condense at least one $C_2+$ alcohol from the alcohol mixture, generating a $C_2+$-rich alcohol fraction and a methanol-rich fraction.

In some embodiments, in addition to the purification unit, the apparatus includes a recirculation unit functionally coupled to the catalyst and the purification unit. The recirculation unit recirculates at least a portion of the methanol-rich fraction produced by the purification unit to the catalyst for reaction with synthesis gas.

The invention will now be illustrated with the following non-limiting examples.

EXAMPLES

Comparative Example 1

Dairy manure, including some water used to wash manure from where it was collected, was placed in a stainless steel or Plexiglas fermentation reactor as described in U.S. Pat. No. 5,185,079. The reactors were purchased from Columbia Tech Tank (Kansas City, Mo.). The manure was first fermented in a thermophilic digester at 135° F. No additional microbes were added. The fermentation relied on the flora found in the manure. The reactor was mixed for 2 minutes each hour. At the end of every 8 hours period, the fermentation mixture was mixed, 1/30 of the volume was withdrawn and transferred to a second vessel for mesophilic fermentation, and an equal volume of manure was added to the thermophilic digester. Thus, the average residence time in the thermophilic digester was 10 days.

A second fermenter vessel housed a mesophilic fermentation. The mesophilic fermentation occurred at 95° F. Again no microbes were added, and the fermentation depended on the native flora found in the manure. Both the mesophilic and the thermophilic digesters were approximately 3/4 filled with liquid, with 1/4 of the volume of the vessel being gas head space. The mesophilic fermenter followed an 8-hour cycle time, with (a) 6 hours of reacting, where the mixture was mixed for 2 minutes each hour; (b) 1.5 hours without mixing to allow the solids to settle; (c) 15 minutes decanting "gray water" liquid supernatant equal to 1/54 of the reactor liquid volume; (d) 15 minutes to add a volume from the thermophilic digester equal to the volume of gray water withdrawn. With 1/54 of the volume replaced every 8 hours, the mesophilic reactor had an average residence time of 18 days.

The settled sludge can be periodically removed from the mesophilic reactor, dried, and sold as fertilizer.

Biogas was withdrawn from the head space of both the thermophilic and mesophilic fermenters continuously.

The biogas from the two fermenters was collected. It contained approximately 69-75% methane, and 25-29% carbon dioxide, with the remainder including small amounts of nitrogen and hydrogen sulfide.

The biogas was partially oxidized using an oxygen-starved gas burner to convert the methane to synthesis gas containing primarily CO and $H_2$ in a 1:2 ratio. The carbon dioxide in the biogas is unaffected by the partial oxidation and is present also in the synthesis gas.

To demonstrate the feasibility of alcohol synthesis, a separately obtained synthesis gas sample containing 18% $H_2$, 28% CO, 30% $CO_2$, 15% $CH_4$ and 9% $N_2$ was contacted a nanosized sulfided molybdenum catalyst suspended in heavy machine oil, as described in U.S. Pat. No. 6,248,796, at 200-325° C. and 500-3000 psi. The catalyst produced an alcohol mixture that contained 232 g/l methanol, 126 g/l ethanol, 168 g/l propanol, and 69 g/l butanol and higher alcohols, and approximately 120 g/l water (due to the high $CO_2$ content).

Waste heat from the catalyst was transferred to heat the fermenters, using an ethylene glycol heat transfer medium.

Methane production can be calculated by multiplying the conversion factor 8 cubic feet methane per pound volatile organics, times the volatile organics conversion efficiency. The conversion efficiency of volatile organics in the substrate for the fermentation mixture to biogas was 45-55%, as calculated by the loss of volatile liquid and solid organics. Approximately 6-7 gallons of alcohol mixture was produced per 1000 cubic feet of methane.

Example 1

This example used a single fermenter vessel, which housed a mesophilic fermentation at 95° F. Dairy manure was added to the fermenter as in Comparative Example 1. ATCC 55339 was added to the fermenter at the initiation of fermentation. No other microorganisms were added. The fermenter followed an 8-hour cycle time, with (a) 6 hours of reacting, where the mixture was mixed for 2 minutes each hour; (b) 1.5 hours without mixing to allow the solids to settle; (c) 15 minutes decanting "gray water" liquid supernatant equal to 1/36 of the reactor liquid volume; (d) 15 minutes to add a volume from the thermophilic digester equal to the volume of gray water withdrawn. With 1/36 of the volume replaced every 8 hours, the mesophilic reactor had an average residence time of 12 days. Granulated iron oxide (magnetite) was added to the bioreactor by automatic augur or similar device. Approximately 1/8 of a pound magnetite was added per day per cow.

Despite just a 12-day residence and the lack of a thermophilic digestion, with the iron-reducing bacterium ATCC 55339 added, the volatile organics conversion efficiency was 75-86%. This compares to about 50-65% in comparable conditions without the bacteria.

The biogas was converted to syngas, and the syngas converted to alcohol as in Comparative Example 1.

The gray water removed from the reactor in Example 1 contains phosphate and polymers containing phosphate formed from the manure. Phosphates lead to eutrophication of ground waters, and so should be minimized in discharged wastewaters. However, the gray water also contains $Fe^{2+}$ formed by the iron-reducing microbe. If the gray water is aerated after removal from the fermenter, the ferrous iron is oxidized to ferric, which binds and precipitates the phosphates. The precipitate can be separated out before discharge of the gray water, and can be dried and sold as a phosphate- and iron-rich fertilizer. See U.S. Pat. Nos. 5,667,673; 5,543,049; and 5,620,893.

Example 2

Waste water from a yeast manufacturing facility (growing yeast on sugar beet waste) is digested in anaerobic fermenter as described in Example 1 to generate biogas. Biogas containing 600 scf/hour of methane is produced. An oxygen stream of 300 scf/hour is mixed with the biogas stream, and the gases enter a partial oxidation reactor for reaction at 850° C. at ambient pressure in the presence of a commercial catalyst to form synthesis gas consisting primarily of $H_2$ and CO.

The synthesis gas exits the partial oxidation system and is cooled and compressed.

Synthesis gas is contacted with the ruthenium catalyst whose preparation is described above and in U.S. Pat. No. 4,333,852 at 6,000 psi and 240° C. to produce a product mixture containing ethanol as the most abundant product, substantial methanol, and higher alcohols.

After exiting the reactor, the gas stream is de-pressurized, cooled, and the ethanol and higher ($C_3$+) alcohols condensed and removed. This ethanol-rich alcohol fraction is routed to a storage drum.

Unreacted synthesis gas and reaction by-products (methanol, carbon dioxide, and water) exit the condenser and are scrubbed with $H_2O$ and $CO_2$ scrubbers to remove $H_2O$ and $CO_2$.

Unreacted synthesis gas and methanol are reheated, re-pressurized, and mixed with incoming synthesis gas from the partial oxidation unit. The gas mixture is then recirculated through the alcohol reactor.

All references, patents, and patent documents cited are hereby incorporated by reference.

What is claimed is:

1. A method of producing alcohol comprising:
   fermenting organic material in a fermentation mixture to a biogas comprising methane, wherein the fermentation mixture comprises a microorganism that reduces $Fe^{3+}$ and produces at least one volatile organic acid from organic substrates;
   converting at least a portion of the biogas to synthesis gas comprising CO and $H_2$; and
   contacting at least a portion of the synthesis gas with a catalyst to produce alcohol.

2. The method of claim 1 wherein the microorganism that reduces $Fe^{3+}$ is derived from ATCC 55339.

3. The method of claim 1 wherein the fermentation mixture further comprises an iron source.

4. The method of claim 3 wherein the iron source is magnetite.

5. The method of claim 1 wherein the step of converting at least a portion of the biogas to synthesis gas comprises partially oxidizing at least a portion of the biogas.

6. The method of claim 1 further comprising purifying the alcohol, wherein the purified alcohol comprises less than 0.5% by weight methanol.

7. The method of claim 6 wherein the step of purifying the alcohol comprises fractionating the alcohol into a $C_2+$-rich fraction and a methanol-rich fraction, wherein the method further comprises recirculating the methanol-rich fraction into the synthesis gas for contact with the catalyst.

8. The method of claim 1 further comprising purifying the alcohol wherein the purified alcohol comprises at least 60% by weight ethanol.

9. The method of claim 1 wherein the contacting step produces heat that is used to heat the fermentation mixture.

10. The method of claim 1 wherein the iron-reducing microorganism produces $Fe^{2+}$ that binds sulfhydryls in the fermentation mixture.

11. The method of claim 1 wherein the step of fermenting organic material to a biogas comprises the steps of feeding the organic material into a vessel, fermenting and mixing the organic material in anaerobic conditions in the vessel to form the biogas, discontinuing the mixing to allow particulate unfermented organic material to settle in the vessel resulting in the formation of a low-suspended-solid supernatant, decanting the supernatant from the vessel, and repeating at least the feeding and fermenting steps.

12. The method of claim 11 further comprising withdrawing at least a portion of the biogas from the vessel immediately before the settling.

13. The method of claim 1 wherein the organic material comprises dairy manure.

14. The method of claim 1 wherein the organic material comprises hog manure, turkey manure, chicken manure, slaughterhouse waste, municipal sewage, or crop waste.

15. The method of claim 14 wherein the organic material comprises crop waste, wherein the crop waste is sugar beet waste.

16. The method of claim 1 wherein the organic material comprises forest products waste.

17. The method of claim 1 wherein the alcohol comprises $C_2+$ alcohols, the yield of $C_2+$ alcohols is at least 6 gallons per 1000 cubic feet of methane in the biogas, and the conversion of volatile organics in the fermentation mixture to biogas is at least 65% efficient.

18. The method of claim 10 wherein the catalyst is sulfur-free and the alcohol comprises less than 10 ppm sulfur atoms.

19. The method of claim 18 wherein the alcohol comprises less than 1 ppm sulfur atoms.

20. The method of claim 18 wherein the method further comprises contacting the biogas with a sulfur scrubber separate from the $Fe^{2+}$ produced by the iron-reducing microorganism.

* * * * *